(12) United States Patent
So et al.

(10) Patent No.: US 9,161,981 B2
(45) Date of Patent: Oct. 20, 2015

(54) NON-AQUEOUS OILY INJECTABLE FORMULATION EXHIBITING PRESERVATIVE EFFICACY

(75) Inventors: Jin Eon So, Daejeon (KR); Dong Jun Yeo, Daejeon (KR); Yoon-Seon Jang, Daejeon (KR)

(73) Assignee: LG LIFE SCIENCES, LTD., Seoul (KR)

( * ) Notice: Subject to any disclaimer, the term of this patent is extended or adjusted under 35 U.S.C. 154(b) by 0 days.

(21) Appl. No.: 13/820,698

(22) PCT Filed: Sep. 9, 2011

(86) PCT No.: PCT/KR2011/006707
§ 371 (c)(1),
(2), (4) Date: Mar. 25, 2013

(87) PCT Pub. No.: WO2012/036430
PCT Pub. Date: Mar. 22, 2012

(65) Prior Publication Data
US 2013/0210729 A1    Aug. 15, 2013

(30) Foreign Application Priority Data
Sep. 16, 2010 (KR) .................. 10-2010-0091036

(51) Int. Cl.
| | | |
|---|---|---|
| *A61K 47/10* | (2006.01) | |
| *A61K 9/00* | (2006.01) | |
| *A61K 31/728* | (2006.01) | |
| *A61K 47/14* | (2006.01) | |

(52) U.S. Cl.
CPC .............. *A61K 47/10* (2013.01); *A61K 9/0019* (2013.01); *A61K 31/728* (2013.01); *A61K 47/14* (2013.01)

(58) Field of Classification Search
None
See application file for complete search history.

(56) References Cited

U.S. PATENT DOCUMENTS

| 7,109,161 | B1 | 9/2006 | Gayed | |
|---|---|---|---|---|
| 7,432,360 | B2 | 10/2008 | Gayed | |
| 2005/0118206 | A1 | 6/2005 | Luk et al. | |
| 2005/0287180 | A1 | 12/2005 | Chen | |
| 2007/0078084 | A1* | 4/2007 | Kishore et al. | 514/12 |
| 2007/0249730 | A1* | 10/2007 | Daftary et al. | 514/731 |
| 2007/0264349 | A1* | 11/2007 | Lee et al. | 424/489 |

OTHER PUBLICATIONS

Kim et al. J Korean Med Sci 2010; 25;776-80.*
Microbac Laboratories, Inc. USP Antimicrobial Effectiveness Testing. 2011.*
International Search Report issued in PCT/KR2011/006707, mailed on Apr. 6, 2012.
Written Opinion of the International Searching Authority issued in PCT/KR2011/006707, mailed on Apr. 6, 2012.

* cited by examiner

*Primary Examiner* — Amber D Steele
*Assistant Examiner* — Schuyler Milton
(74) *Attorney, Agent, or Firm* — Birch, Stewart, Kolasch & Birch, LLP

(57) ABSTRACT

Disclosed herein is preferably a multi-dose type non-aqueous oily injectable formulation including; an active ingredient (drug) expressing therapeutic effects, which is dissolved, dispersed or suspended in a therapeutically effective amount, in oil. The disclosed non-aqueous oily injectable formulation may include; an oil-affinitive preservative, and a hydrophilic excipient non-phase separable from the oil-affinitive preservative when the excipient is mixed with the oil-affinitive preservative.

17 Claims, No Drawings

NON-AQUEOUS OILY INJECTABLE FORMULATION EXHIBITING PRESERVATIVE EFFICACY

TECHNICAL FIELD

The present invention relates to an injectable formulation including a therapeutically effective amount of an active ingredient, an oil containing the active ingredient, a hydrophilic excipient non-phase separable from the oil and/or an oil-affinitive (commonly referred to as 'lipophilic') preservative combined with the hydrophilic excipient, which may exhibit higher preservative efficacy, compared to administration of the preservative alone.

BACKGROUND ART

In the case where a medication does not have suitable anti-microbial activity, an injectable formulation containing the medication should be provided with an anti-microbial preservative or any suitable additive, to prevent proliferation or contamination of microorganisms.

Specifically, a multiple-dose injection may be a formulation wherein the injection is drawn (or extracted) several times from a vial or, otherwise, an injection needle is stuck in a cartridge several times, thus being used. In order to prepare against contamination of the microorganisms possibly occurring while repeatedly using, high antimicrobial activity is needed.

Although numerous studies and investigations into aqueous injectable formulations having improved preservative abilities have been implemented, a non-aqueous injectable formulation with high preservative ability has yet to be disclosed.

DISCLOSURE OF INVENTION

Technical Problem

The present inventors have conducted extensive and intensive studies and various experiments and found that an injectable formulation with specific constitutional composition as described below according to the present invention may surprisingly exhibit higher preservative ability, compared to administration of a lipophilic preservative alone, thereby completing the present invention.

Solution to Problem

Accordingly, the present invention provides an injectable formulation that includes a physiologically effective amount of active ingredient, oil containing the active ingredient, a hydrophilic excipient non-phase separable from the oil, and a lipophilic preservative combined with the hydrophilic excipient, which exhibits higher preservative ability (hereinafter, referred to as 'preservative efficacy'), compared to administration of the lipophilic preservative alone.

The injectable formulation is usually used in cases where a desired level of efficacy of the medication should be rapidly attained, the medication cannot be orally administered, the medication is modified by digestive juices or less absorbed, and/or the medication stimulates mucosa of gastrointestinal tract (GI tract), and may be directly administrated via intradermal, subcutaneous, intramuscular, intravenous or intraarterial routes. Such an injectable formulation should be sterile and a multi-dose formulation must have preservative efficacy to maintain a sterile condition over the period of use.

Specifically, a non-aqueous oily injectable formulation may be a formulation that is used as a solvent for dissolving a water-insoluble drug or, otherwise, adopts oil as a medium for dispersing or suspending an active ingredient in a powder form, which is insoluble in the oil. A multi-dose injectable formulation based on the foregoing must ensure high preservative efficacy and, therefore, may have advantages of enabling repetitive administration to thus improve convenience in use and reducing waste of drug and/or receptacles for drugs. However, careful attention to stability and storage of the formulation is necessary.

Hereinafter, the present invention will be described in more detail.

An active ingredient in a therapeutically effective amount may be a protein or peptide drug and hyaluronic acid or an inorganic salt thereof. Another examples of the active ingredient may include; testosterone ester, progesterone ester, haloperidol ester, nandrolone decanoate, boldenone undecylenate, etc., without being particularly limited thereto.

The active ingredient described in the present invention may be included in oil. More particularly, the active ingredient may be dissolved, dispersed or suspended in oil, however, such a way of including the active ingredient in the oil is not particularly limited to the foregoing.

According to one preferred embodiment, the active ingredient may be present in a particle form covered with a lipophilic material on the surface thereof and dispersed or suspended in oil. Such a lipophilic material may be selected from a group consisting of lipids, lipid derivatives, fatty acid, fatty acid salts, fatty acid ester derivatives, other fatty acid derivatives, surfactants, lecithin, hyaluronic acid and waxes. In this regard, the content of Korean Patent No. 0329336 owned by the present applicant, is incorporated by reference.

The term 'therapeutically effective amount' means an amount of a drug administered to alleviate or reduce at least one or more of symptoms of a disorder to be treated using the drug, or an amount of an active ingredient effective to delay initiation of clinical markers or symptoms of a disease to be prevented. That is, the therapeutically effective amount practically means an amount expressing: (1) inversion effects of the progress of disease; (2) inhibitory effects of the progress of disease over a certain extent; and/or (3) effects of moderately alleviating (preferably eliminating) at least one or more symptoms related to a disease. The therapeutically effective amount may be determined from empirical results by testing a compound in vivo and/or in vitro model systems.

According to the present invention, the oil may be a solvent in which the active ingredient is dissolved, dispersed and/or suspended and may include, for example; monoglyceride, diglyceride, triglyceride, medium chain triglyceride (MCT), sesame oil, *Arachis* oil (peanut oil), castor oil, olive oil, corn oil, cotton seed oil, soybean oil, peppermint oil, coconut oil, palm seed oil, safflower oil, etc., without being particularly limited thereto. These substances may be used alone or as a mixture of two or more thereof.

According to the present invention, a lipophilic preservative is a component preventing degeneration and/or decomposition of an injectable formulation, that is, is added to prevent decomposition of animal/vegetable organic substances by activity of microorganisms. The preservative must be harmless to a human body and efficacy and/or toxicity of an active ingredient must not be varied or altered by adding the preservative.

Preservatives used for a water-soluble injectable formulation as a major type of injections may include, for example; phenol, m-cresol, benzyl alcohol, methyl paraben, propyl paraben, penzalkonium chloride, thiomerosal, chlorobutanol, phenoxyethanol, and so forth. However, in the case where a non-aqueous oily injectable formulation according to the present invention includes a preservative normally used for a water-soluble injectable formulation, it is difficult to attain preservative efficacy substantially equal to that of the water-soluble injectable formulation.

The lipophilic preservative useable in the present invention may be at least one selected from a group consisting of, for example; phenol, m-cresol, benzyl alcohol, methyl paraben, propyl paraben, penzalkonium chloride, thiomerosal, chlorobutanol, ethanol, phenoxyethanol and phenoxyethanol, without being particularly limited thereto.

A content of the lipophilic preservative may range from 0.01 to 20% (w/v) in relation to a total weight of the formulation. In the case where the content is too low, it is difficult to attain preservative effects. On the contrary, if the content is too high, toxic effects may be exhibited, thus not being preferable. More preferably, the content ranges from 0.1 to 10% (w/v) and, most preferably, 0.1 to 5% (w/v).

A hydrophilic excipient used herein means an excipient combined with the lipophilic preservative and enabling contact between a water phase, in which microorganisms are present, and the lipophilic preservative. Practical examples of the hydrophilic excipient may be at least one selected from a group consisting of; propyleneglycol, polyethyleneglycol, polypropyleneglycol, glycerol, acetic acid, citric acid, dimethylsulfoxide (DMSO), N-methylpyrrolidone (NMP) and dimethylacetamide (DMA), without being particularly limited thereto.

Propyleneglycol as a hydrophilic excipient is an excipient generally used as a co-solvent for increasing drug solubility in an aqueous solution type formulation and/or an emulsion formulation. Propyleneglycol also known to have preservative efficacy may be used as a disinfectant. However, in order to use propyleneglycol as a preservative component of the aqueous solution type injectable formulation, this must be applied at high concentration. Therefore, it is known that propyleneglycol has a difficulty in use as a typical preservative in an injectable formulation for directly administering a drug solution to blood, subcutaneous tissue, skin or muscle. However, according to the present invention, it was surprisingly identified that, even adding a small amount of propyleneglycol together with a lipophilic preservative to a non-aqueous injectable formulation, preservative efficacy of the formulation may be enhanced.

As other examples of the hydrophilic excipient, polyethyleneglycol may have a number average molecular weight ranging from 200 to 10,000,000 while polypropyleneglycol may have a number average molecular weight of 200 to 5,000.

A content of the foregoing hydrophilic excipient may range from 0.01 to 20% (w/v) in relation to a total weight of the formulation. In the case where the content is too low, it is difficult to attain synergic effects of preservative efficacy. On the contrary, if the content is too high, toxic effects may be exhibited or phase separation may occur, thus not being preferable. More preferably, the content ranges from 0.1 to 10% (w/v) and, particularly preferably, 0.1 to 5.0% (w/v).

The injectable formulation of the present invention may have high preservative efficacy. In general, microorganisms may barely survive in a non-aqueous oily formulation with lack of water, that is, in a low water activity state. However, in the case where the injectable formulation is introduced together with trace of water surrounding microorganisms, some may occasionally survive depending upon types of the microorganisms. Specifically, S. aureus, A. niger, P. aeruginosa, C. albicans, or the like, seldom die but maintain a constant number of individuals or extremely slowly die.

In view of characteristics of an injectable formulation for direct administration of a drug solution into blood, subcutaneous tissue, skin or muscle, the injectable formulation needs higher preservative efficacy, than a level at which microorganisms are not grown and which is substantially not satisfactory for use.

Accordingly, the present invention is characterized in that a lipophilic preservative may be in contact with a water phase containing microorganisms introduced therein by combining the lipophilic preservative with a hydrophilic excipient, thus attaining excellent preservative efficacy, compared to using the lipophilic preservative alone. More particularly, preservative efficacy of the injectable formulation according to the present invention (abbrev. to 'inventive formulation') may mean that, when adding $10^5$ to $10^6$ bacteria to 1 ml or 1 g of the inventive formulation, the number of bacteria is reduced to $10^3$ to $10^4$ or less after 6 hours. Otherwise, the preservative efficacy may mean that, when $10^5$ to $10^6$ bacteria are added to 1 ml or 1 g of the inventive formulation, the number of bacteria is reduced to $10^4$ to $10^5$ or less after 7 days. In this regard, the bacteria may be S. aureus, P. aeruginosa, E. coli, etc., without being particularly limited thereto.

As the preservative efficacy attained by the present invention is expressed with reference to fungi, it may mean that the number of fungi is reduced to $10^5$ or $10^6$ or less after 7 days when $10^5$ to $10^6$ fungi are added to 1 mg or 1 g of the inventive formulation. Otherwise, the foregoing may mean that the number of fungi is reduced to $10^3$ to $10^4$ or less after 7 days when $10^5$ to $10^6$ fungi are added to 1 mg or 1 g of the inventive formulation. In this case, such fungi may be A. niger, C. albicans, etc., without being particularly limited thereto.

In this regard, a partition coefficient 'P' of partition between a non-aqueous oil phase and a water phase containing microorganisms therein, may become a criterion to determine preservative efficacy. The partition coefficient P is a value calculated by dividing a concentration of preservative in the oil phase by a concentration of preservative in the water phase. If the partition coefficient is high, the concentration of preservative in the oil phase is increased, thus causing a difficulty in attaining preservative effects. In contrast, if the partition coefficient is low, distribution between the oil phase and the water phase may be improved, thus expecting sufficient preservative effects even in the water phase. Accordingly, the lower the partition coefficient, the higher the preservative efficacy of the oil formulation to bacteria or fungi living in the water phase may be considered.

Such a partition coefficient may be considerably varied depend upon kinds of oil and/or preservative. For instance, in the case where the partition coefficient is measured by using medium chain triglyceride (MCT) as oil and phenol as a preservative, which is most frequently used in the art, the measured partition coefficient may be about 13.7, in turn being 1.1 in respects to Log P. This means that a concentration of phenol present in the water phase is only 1/13.7 of a concentration of phenol present in the oil phase, thus causing a difficulty in attaining desired preservative efficacy.

For a formulation that does not contain a hydrophilic excipient used in the present invention, since the partition coefficient is very high, a concentration of the lipophilic preservative in the water phase is considerably decreased. In contrast, the formulation containing the hydrophilic excipient shows increased concentration in the water phase.

A multi-dose type non-aqueous oily injectable formulation according to the present invention may include a lipophilic preservative and a hydrophilic excipient, both of which have different affinities to oil, and exhibit non-phase separation of the hydrophilic excipient from the oil.

Phase separation occurring between the lipophilic preservative and the hydrophilic excipient may be partially varied depending upon kinds of materials used for combination of the foregoing substances and contents thereof. The reason for this is presumed that inherent characteristics of individual components in a specific combination of the lipophilic preservative and the hydrophilic excipient may mutually influence one another. Accordingly, based on overall description of the present invention as described above, there is no difficulty to suitably determine contents and content ratios of non-phase separable lipophilic preservative and hydrophilic excipient by those skilled in the related art, through repeated experimentation of selected substances. Although one embodiment of the foregoing is proposed as Comparative Example 1 below, the scope of the present invention is not particularly limited thereto.

According to one preferred embodiment, a content ratio of a lipophilic preservative and a hydrophilic excipient may be slightly varied depending upon types of materials used. However, generally considering expression of improved preservative efficacy, inhibition of phase separation, or the like, the content ratio may range from 1:10 to 10:1 in terms of ratio by weight.

According to an exemplary embodiment, an injectable formulation of the present invention may be a formulation comprising; 0.1 to 100 mg/ml of hGH, 0.1 to 1.5% w/v of propyleneglycol and 0.1 to 1% w/v of phenol suspended in a medium chain triglyceride (MCT).

Of course, a non-aqueous oily injectable formulation according to the present invention may further include other components known in the related art.

Advantageous Effects of Invention

A non-aqueous oily injectable formulation according to the present invention does not show phase separation, is stable, and exhibits very high preservative efficacy. Consequently, the inventive formulation may be effectively used as an injectable formulation, specifically, a multi-dose type non-aqueous oily injectable formulation.

MODE FOR THE INVENTION

Hereinafter, preferred embodiments of the present invention will be described in detail by the following examples, however, the scope of the present invention is not particularly limited to such examples.

With reference to The European Pharmacopoeia and The US Pharmacopoeia, a method of assaying preservative efficacy was executed while focusing on S. aureus and A. niger with strong survival characteristics, among a variety of bacteria and fungi.

Experiments to identify whether typical preservatives used for medication exhibit preservative efficacy refer to preservative efficacy tests (PETs). Such a PET is to determine a variation in number of individuals of microorganisms over time, after adding the microorganisms to a formulation containing the preservative to reach $10^5$ to $10^6$ per 1 ml or 1 g of the formulation. PETs are representatively stated in The European Pharmacopeia (EP 5.1.3 Efficacy of Antimicrobial Preservation) and The US Pharmacopoeia (USP 51 Antimicrobial Effectiveness Testing).

The present invention will be better understood from the following examples and comparative examples.

Comparative Example 1

Test for Measurement of Phase Stability by Preservative

An experiment was executed to identify whether a formulation is separated into an oil phase and a water phase in the case where the formulation is stored at 5° C., as a predetermined storage condition, for several days. Results of the experiment are shown in Table 1 below. In the following table, the content was expressed in units of % by weight (w/v).

TABLE 1

| Phase stability along with preservative | | | |
|---|---|---|---|
| | Preservative | Propyleneglycol | Phase separation |
| Phenol/propyleneglycol composite formulation | 0.3% phenol | 0.9% propyleneglycol | Non-phase separation |
| | 0.3% phenol | 1% propyleneglycol | Phase separation |
| Ethanol/propyleneglycol composite formulation | 1% ethanol | 1% propyleneglycol | Non-phase separation |
| | 1% ethanol | 2% propyleneglycol | Phase separation |
| Benzyl alcohol/ propyleneglycol composite formulation | 1.5% benzyl alcohol | 1% propyleneglycol | Non-phase separation |
| | 1.5% benzyl alcohol | 1.5% propyleneglycol | Phase separation |

As shown in the above Table 1, phase separation was varied depending upon concentrations of propyleneglycol and the preservative, thus demonstrating that the constitutional composition at which phase separation occurred is not suitable for an injectable formulation.

Comparative Example 2

Preservative Efficacy by Addition of Hydrophobic Preservative to Non-Aqueous Oily Formulation In this present experiment, preservative efficacy of a preservative was assayed in the case where a preservative such as phenol, cresol, benzyl alcohol, chlorobutanol, etc., commonly available in injectable formulations, was used alone in MCT oil.

More particularly, after dissolving a preservative in MCT as non-aqueous oil, a preservation test was executed under the conditions listed in Table 2 below, according to test methods in The European Pharmacopoeia ('EP') and/or The US Pharmacopoeia ('USP'). Measurement of the number of microorganisms during the preservation test was conducted by a membrane filtration method. More particularly, $1 \times 10^5$ to $1 \times 10^6$ CFU/mL of each strain was added to a sample to reach 1% (v/v), followed by flowing the sample through a 0.45 μm cellulose nitrate filter. The filter was washed three times, using 100 mL of a sodium chloride-peptone buffer (pH 7.0). For bacteria culture, the filter was moved to Trypticase soy agar. On the other hand, for culturing fungi, the filter was moved to Sabouraud dextrose agar. The bacteria were cultured at 30 to 35° C. while the fungi were cultured at 20 to 25° C., respectively, for 5 days. From the respective cultured products, strains were counted and Log reduction values thereof were estimated. In order to appropriately conduct the filtering and dilution, a solution prepared by dissolving a surfactant, that is, polysorbate 80 in a saline solution to a concentration of 10% was used as a dilute solution at initial dilution. The dilute solution was then diluted 1000 times to obtain a uniform solution. Additional dilution was implemented using a saline solution to be diluted by 10 fold. Hereinafter, the preservation tests in the following examples have been executed according to the present test procedures, unless otherwise stated.

Test results are shown respectively in Tables 3 and 4 below.

TABLE 2

Formulation containing preservative only added to MCT oil

| Formulation No. | Oil | Preservative |
|---|---|---|
| 1 | MCT | None |
| 2 | MCT | 0.5% (w/v) phenol |
| 3 | MCT | 1.5% benzyl alcohol |
| 4 | MCT | 0.5% m-cresol |
| 5 | MCT | 0.5% chlorobutanol |

TABLE 3

Preservative efficacy of formulation containing preservative only added to MCT oil (S. aureus)

| | Log Reduction | | | |
|---|---|---|---|---|
| Formulation No. | 6 hours | 24 hours | 7 days | 14 days |
| 1 | 0.2 | 0.4 | 1.6 | 2.0 |
| 2 | 0.0 | <1 | 1.8 | — |
| 3 | 0.5 | 1.0 | 1.9 | — |
| 4 | 0.9 | 1.2 | <2 | — |
| 5 | 0.2 | 0.4 | 1.4 | — |

TABLE 4

Preservative efficacy of formulation containing preservative only added to MCT oil (A. niger)

| | Log Reduction | |
|---|---|---|
| Formulation No. | 7 days | 14 days |
| 1 | 0 | 0 |
| 2 | 0 | 0.1 |
| 3 | 0.2 | 0.3 |
| 4 | 0.1 | 0 |
| 5 | — | — |

As shown in the above Tables 3 and 4, for both *S. aureus* and *A. niger*, a formulation containing a preservative added thereto did not impart noticeable variation, as compared to a formulation without a preservative. Such results demonstrate that the lipophilic preservatives such as phenol, cresol, benzyl alcohol, chlorobutanol, etc., did not sufficiently function as the preservative in the MCT oil as a non-aqueous solution.

Example 1

Effect of Propyleneglycol (PG) in Non-Aqueous Oily Formulation

The present experiment was executed to identify effects of a formulation comprising a mixture of a hydrophobic preservative and a hydrophilic excipient.

As shown in Table 5 below, propyleneglycol was suitably mixed with ethanol, phenol and benzyl alcohol to prepare a formulation. Although propyleneglycol itself is immiscible with MCT oil, this may be miscible with MCT if mixed with phenol, benzyl alcohol, ethanol, etc. in an appropriate relative ratio. Considering influence of temperature, the mixing ratio may be determined by selecting two individual formulations having appropriate constitutional compositions at which the foregoing two formulations can be mixed well while not becoming cloudy (or turbid) even though the prepared formulation is stored at 5° C. for several days.

The foregoing formulations were subjected to preservation tests and test results thereof are shown in Tables 6 and 7.

TABLE 5

Formulation containing propyleneglycol as well as preservative added to MCT oil

| Formulation No. | Oil | Additive (%(w/v)) |
|---|---|---|
| 6 | MCT | 0.75% propyleneglycol(PG) + 0.3% phenol |
| 7 | MCT | 1% propyleneglycol(PG) + 1.5% benzyl alcohol |
| 8 | MCT | 1% propyleneglycol(PG) + 2% ethanol |

TABLE 6

Preservative efficacy of formulation containing propyleneglycol as well as preservative added to MCT oil (S. aureus)

| | Log Reduction | | | |
|---|---|---|---|---|
| Formulation No. | 6 hours | 24 hours | 7 days | 14 days |
| 6 | N/R | N/R | N/R | — |
| 7 | N/R | N/R | N/R | — |
| 8 | N/R | N/R | N/R | — |

N/R: No recover

TABLE 7

Preservative efficacy of formulation containing propyleneglycol as well as preservative added to MCT oil (A. niger)

| | Log Reduction | |
|---|---|---|
| Formulation No. | 7 days | 14 days |
| 6 | N/R | N/R |
| 7 | N/R | N/R |
| 8 | N/R | N/R |

N/R: No recover

As identified from the above Tables 6 and 7, the formulation comprising propyleneglycol mixed with ethanol, phenol and/or benzyl alcohol exhibited very high preservative efficacy. The reason for this is considered to be because propyleneglycol moves into a microorganism phase and maintains a very high concentration in a micro-environment, thereby expressing preservative efficacy of propyleneglycol itself. Moreover, it is presumed that, as a concentration of propyleneglycol is increased, an increase in osmotic pressure in the micro-environment and, in addition, an increase in concentration (of the preservative) due to variation in a partition coefficient, may also influence the foregoing results.

Example 2

Preservative Efficacy of Other Hydrophilic Excipients in Non-Aqueous Oily Formulation The present experiment was executed according to the same procedures as described in Example 1, except that propyleneglycol was replaced with polyethyleneglycol (PEG 300) and polypropyleneglycol (PPG 400) (see Table 8 below).

Results thereof are shown in Tables 9 and 10 below.

TABLE 8

Formulation containing preservative and PEG300 or the like added to MCT oil

| Formulation No. | Oil | Additive (%(w/v)) |
|---|---|---|
| 9 | MCT | 1% polyethyleneglycol(PEG 300) + 0.5% phenol |
| 10 | MCT | 1% polyethyleneglycol(PEG 300) + 1.5% benzyl alcohol |
| 11 | MCT | 1% polyethyleneglycol(PEG 300) + 2% ethanol |
| 12 | MCT | 5% polypropyleneglycol(PPG 400) + 0.5% phenol |

TABLE 9

Preservative efficacy of formulation containing preservative and PEG300 or the like added to MCT oil (*S. aureus*)

| Formulation No. | Time (Duration) | | | |
|---|---|---|---|---|
| | 6 hours | 24 hours | 7 days | 14 days |
| 9 | 1.5 | N/R | — | — |
| 10 | 2.3 | N/R | — | — |
| 11 | >2 | N/R | — | — |
| 12 | N/R | N/R | — | — |

N/R: No recover

TABLE 10

Preservative efficacy of formulation containing preservative and PEG300 or the like added to MCT oil (*A. niger*)

| Formulation No. | Time (Duration) | |
|---|---|---|
| | 7 days | 14 days |
| 9 | 2.4 | 3.7 |
| 10 | N/R | N/R |
| 11 | 2.7 | 2.9 |
| 12 | 4.4 | N/R |

N/R: No recover

As confirmed from results in the above Tables 9 and 10, formulations comprising polyethyleneglycol mixed with ethanol, phenol, benzyl alcohol, etc., as well as a formulation comprising polypropyleneglycol mixed with phenol, exhibited very high preservative efficacy. Like propyleneglycol described in Example 1, the reason for the foregoing is considered that, as a concentration of a co-solvent is increased in the micro-environment, osmotic pressure is increase and, in addition, a concentration (of the preservative) around microorganisms is increased due to variation in partition coefficient.

Example 3

Preservative Efficacy in Slow Release Type Human Growth Hormone Contained in Non-Aqueous Oil The present experiment was executed to test preservative efficacy of an extended-release (or slow release) type formulation containing human growth hormone (SR-hGH) which was prepared by spray drying and suspended in MCT to reach 100 mg/ml in terms of a powder form.

More particularly, Tween 80 as a surfactant was added in an amount of 0.01 wt. %, in relation to a total weight of a buffer solution, to 5 mM of a phosphate buffer solution containing human growth hormone dissolved with a concentration of 2 mg/ml therein. 2 mg/ml of sodium hyaluronate having a molecular weight of 1,000,000 was dissolved in the foregoing solution to prepare a final solution. The final solution was fed at a flow rate of 3 ml/min into a spray dryer (Buchi 190), thus forming microfine particles. In this regard, a temperature of dried air flowing into the spray dryer was 85° C. while the formed microfine particles had an average particle diameter of 3 μm. 5 g of the sodium hyaluronate microfine particles containing human growth hormone was dispersed in 500 ml of ethanol containing lecithin dissolved with a concentration of 10 mg/ml therein to thus obtain a dispersion. The dispersion was fed into a spray dryer (Buchi 190), thereby forming microfine particles coated with lecithin and having an average particle diameter of 7 μm. In this case, the kinds of additives used herein and contents thereof are shown in Table 11 below.

TABLE 11

SR-hGH suspension formulation

| Formulation No. | Oil | Microfine particles | Additive (%(w/v)) |
|---|---|---|---|
| 13 | MCT | SR-hGH | None |
| 14 | MCT | SR-hGH | 0.75% propyleneglycol(PG) + 0.3% phenol |
| 15 | MCT | SR-hGH | 1% propyleneglycol(PG) + 1.5% benzyl alcohol |
| 16 | MCT | SR-hGH | 1% propyleneglycol(PG) + 2% ethanol |

Based on the foregoing description, tests were executed upon a variety of microorganisms and results thereof are shown in Tables 12 to 16 below.

TABLE 12

Preservative efficacy of SR-hGH suspension formulation (*S. aureus*)

| Formulation No. | Log Reduction | | | |
|---|---|---|---|---|
| | 6 hours | 24 hours | 7 days | 14 days |
| 13 | 0.1 | 0.4 | 1.3 | 2.4 |
| 14 | 3.3 | 3.7 | 4.0 | — |
| 15 | 3.1 | 3.8 | N/R | — |
| 16 | 4.1 | N/R | N/R | — |

N/R: No recover

TABLE 13

Preservative efficacy of SR-hGH suspension formulation (*P. aeruginosa*)

| Formulation No. | Log Reduction | | | |
|---|---|---|---|---|
| | 6 hours | 24 hours | 7 days | 14 days |
| 13 | — | — | — | — |
| 14 | N/R | N/R | — | — |
| 15 | — | — | — | — |
| 16 | N/R | N/R | — | — |

N/R: No recover

TABLE 14

Preservative efficacy of SR-hGH suspension formulation (*E. coli*)

| Formulation No. | Log Reduction | | | |
|---|---|---|---|---|
| | 6 hours | 24 hours | 7 days | 14 days |
| 13 | — | — | — | — |
| 14 | N/R | N/R | — | — |

N/R: No recover

TABLE 15

Preservative efficacy of SR-hGH suspension formulation (*A. niger*)

| Formulation No. | Log Reduction | |
|---|---|---|
| | 7 days | 14 days |
| 13 | 0 | 0.1 |
| 14 | 2.0 | — |
| 15 | >2.0 | — |
| 16 | 3.1 | N/R |

N/R: No recover

TABLE 16

Preservative efficacy of SR-hGH suspension formulation (*C. albicans*)

| Formulation No. | Log Reduction | |
|---|---|---|
| | 7 days | 14 days |
| 13 | 0.8 | 1.6 |
| 14 | N/R | — |
| 15 | — | — |
| 16 | N/R | — |

N/R: No recover

From the above Tables 12 to 16, it can be seen that formulations comprising propyleneglycol mixed with preservatives (Formulations 14 to 16) exhibited excellent preservative efficacy, compared to the formulation without containing a preservative (Formulation 13).

Example 4

Preservative Efficacy in Oil Other than MCT

The present experiment was executed to identify whether a preservative system developed according to the present invention may be applied to oils other than MCT. Sesame oil and peanut oil, respectively, were mixed with propyleneglycol and phenol to prepare formulations, in turn forming SR-hGH suspensions, as described in Example 3. Preservative efficacy of each of the obtained suspensions was compared to formulations without preservatives. In this case, the kinds of oils used herein and contents of additives are shown in Table 17 below.

TABLE 17

Formulation containing other oil as a substitute for MCT

| Formulation No. | Oil | Microfine particles | Additive (%(w/v)) |
|---|---|---|---|
| 17 | Sesame oil | SR-hGH | None |
| 18 | Sesame oil | SR-hGH | 0.75 propyleneglycol + 0.3% phenol |
| 19 | Peanut oil | SR-hGH | None |
| 20 | Peanut oil | SR-hGH | 0.75 propyleneglycol + 0.3% phenol |

TABLE 18

Preservative efficacy of formulation containing other oil as a substitute for MCT (*S. aureus*)

| Formulation No. | Log Reduction | | | |
|---|---|---|---|---|
| | 6 hours | 24 hours | 7 days | 14 days |
| 17 | 1.0 | <1.0 | — | — |
| 18 | 3.6 | 3.9 | — | — |
| 19 | 1.9 | 2.4 | — | — |
| 20 | 3.1 | 4.2 | — | — |

As shown in the above Table 18, it was confirmed that the preservative composed of phenol and propyleneglycol, which are mixed with MCT in previous example also exhibits excellent preservative efficacy in sesame oil and peanut oil, respectively, as non-aqueous solutions other than MCT.

Example 5

Preservative Efficacy Along with Concentration of Propyleneglycol

In the present example, formulations were prepared by fixing a concentration of phenol as a lipophilic preservative to 0.3% while varying a concentration of propyleneglycol in the range of less than 1%, as shown in Table 19 below. For the prepared formulations, preservation tests were executed and results thereof are shown in Table 20 below.

TABLE 19

SR-HGH suspension formulation with varied concentrations of propyleneglycol therein

| Formulation No. | Oil | SR-hGH | Additive (%(w/v)) |
|---|---|---|---|
| 17 | MCT | 20 mg/ml | 0.6% propyleneglycol + 0.3% phenol |
| 18 | MCT | 20 mg/ml | 0.7% propyleneglycol + 0.3% phenol |
| 19 | MCT | 20 mg/ml | 0.8% propyleneglycol + 0.3% phenol |

TABLE 20

SR-HGH suspension formulation with varied concentrations of propyleneglycol therein

| Formulation No. | Time (Duration) | | |
|---|---|---|---|
| | 6 hours | 24 hours | 7 days |
| 17 | 1.8 | 2.0 | 2.5 |
| 18 | 2.9 | 3.4 | — |
| 19 | 2.5 | 3.4 | 4.1 |

As shown in the above Table 20, it can be seen that excellent preservative efficacy is exhibited in the range of concentration of the propyleneglycol of less than 1%.

Example 6

Measurement of Content of Preservative in Water Phase

A formulation was prepared by adding phenol alone to MCT oil to reach 0.5%, while another formulation was prepared by further adding polypropyleneglycol (PPG 400) to reach 5%. Then, after feeding oil and a saline solution in a ratio of 19:1 to the formulation and sufficiently mixing the same, an amount of phenol contained in each phase was quantified through HPLC to calculate a partition coefficient. Results thereof are shown in Table 21 below.

TABLE 21

Variation in partition coefficient by addition of polypropyleneglycol

| Formulation | | Partition coefficient (P) | logP |
|---|---|---|---|
| 9.5 ml MCT (0.5% (w/v) phenol) | 0.5 ml saline | 13.7 | 1.1 |
| 9.5 ml MCT (0.5% phenol, PPG 400) | 0.5 ml saline | 0.8 | −0.1 |

Partition coefficient (P) = phenol concentration of oil phase/phenol concentration of saline phase As shown in the above Table 21, the formulation without polypropyleneglycol showed too high a partition coefficient, thus having a very low phenol concentration in a saline phase. On the contrary, the formulation containing polypropyleneglycol exhibited a relatively high concentration of polypropyleneglycol in the saline phase. As a result, it can be seen that a concentration of phenol, that is, the preservative, in the saline phase is increased, thus increasing preservative efficacy of the oily formulation.

As set forth above, a variety of modifications and applications will be possibly made by those skilled in the art to which the present invention pertains, within the scope of the present invention.

The invention claimed is:

1. An injectable formulation, comprising:
a physiologically effective amount of active ingredient;
oil containing the active ingredient;
a hydrophilic excipient non-phase separable from the oil; and
a lipophilic preservative combined with the hydrophilic excipient, which exhibits higher preservative efficacy, compared to administration of the lipophilic preservative alone,
wherein the hydrophilic excipient is at least one selected from the group consisting of propyleneglycol, polyethyleneglycol, polypropyleneglycol, acetic acid, citric acid, dimethylsulfoxide (DMSO), N-methylpyrolidone (NMP) and dimethylacetamide (DMA),
wherein the lipophilic preservative is at least one selected from the group consisting of: phenol, m-cresol, benzyl alcohol, methyl paraben, propyl paraben, penzalkonium chloride, thiomerosal, chlorobutanol, ethanol and phenoxyethanol, and wherein said formulation is an injectable non-aqueous formulation.

2. The formulation according to claim 1, wherein the preservative efficacy is expressed by $10^3$ to $10^4$ or less of bacteria after 6 hours when adding $10^5$ to $10^6$ bacteria to 1 ml or 1 g of the injectable formulation.

3. The formulation according to claim 1, wherein the preservative efficacy is expressed by $10^4$ to $10^5$ or less of bacteria after 7 days when adding $10^5$ to $10^6$ bacteria to 1 ml or 1 g of the injectable formulation.

4. The formulation according to claim 2, wherein the bacteria are S. aureus, P aeruginosa or E. coli.

5. The formulation according to claim 4, wherein the bacteria are S. aurecus.

6. The formulation according to claim 1, wherein the preservative efficacy is expressed by $10^5$ to $10^6$ or less of fungi after 7 days when adding $10^5$ to $10^6$ fungi to 1 ml or 1 g of the injectable formulation.

7. The formulation according to claim 1, wherein the preservative efficacy is expressed by $10^3$ to $10^4$ or less of fungi after 7 days when adding $10^5$ to $10^6$ fungi to 1 ml or 1 g of the injectable formulation.

8. The formulation according to claim 6, wherein the fungi are A. niger or C. albicans.

9. The formulation according to claim 8, wherein the fungi are A. niger.

10. The formulation according to claim 1, wherein the active ingredient is a protein or peptide drug and hyaluronic acid or an inorganic salt thereof.

11. The formulation according to claim 1, wherein the oil is at least one or two or more selected from a group consisting of monoglyceride, diglyceride, triglyceride, medium chain triglyceride (MCT), sesame oil, Arachis oil (peanut oil), castor oil, olive oil, corn oil, cotton seed oil, soybean oil, peppermint oil, coconut oil, palm seed oil and Safflower oil.

12. The formulation according to claim 1, wherein the lipophilic preservative has a concentration of 0.01 to 20% weight/volume (% (w/v)), while the hydrophilic excipient has a concentration of 0.01 to 20% weight/volume (% (w/v)).

13. The formulation according, to claim 1, wherein a ratio by weight of the lipophilic preservative to the hydrophilic excipient ranges from 1:10 to 10:1.

14. The formulation according to claim 1, wherein the injectable formulation is a formulation for multi-dose administration.

15. The formulation according to claim 1, wherein 0.1 to 100 mg/ml of hGH, 0.1 to 1.5% weight/volume (% (w/v)) of propyleneglycol and 0.1 to 1% weight/volume (% (w/v)) of phenol are suspended in MCT.

16. The formulation according to claim 3, wherein the bacteria are S. aureus, P aeruginosa or E. coli.

17. The formulation according to claim 7, wherein the fungi are A. niger or C. albicans.

* * * * *